United States Patent [19]

Battista et al.

[11] Patent Number: 4,851,591
[45] Date of Patent: Jul. 25, 1989

[54] MAGNESIUM-CONTAINING CATALYST ACTIVATED UNDER VACUUM, IN NITROGEN, OR IN AIR, AND USE IN AN ORTHO-ALKYLATION PROCESS

[75] Inventors: Richard A. Battista, Mt. Vernon, Ind.; James G. Bennett, Jr., Glenmont; John J. Kokoszka, Delmar, both of N.Y.; Freddie L. Tungate, Georgetown, Ind.

[73] Assignee: General Electric Company, Selkirk, N.Y.

[21] Appl. No.: 133,748

[22] Filed: Dec. 16, 1987

Related U.S. Application Data

[63] Continuation of Ser. No. 555,714, Nov. 28, 1983, abandoned.

[51] Int. Cl.$^4$ ............................................. C07C 37/16
[52] U.S. Cl. .................................... 568/804; 568/794
[58] Field of Search ............................... 568/804, 794

[56] References Cited

U.S. PATENT DOCUMENTS

| 2,932,673 | 4/1960 | Melik et al. | 568/804 |
| 3,347,936 | 10/1967 | Froitzheim et al. | 568/804 |
| 3,446,856 | 5/1969 | Hamilton | 568/804 |
| 3,479,410 | 11/1969 | Hamilton | 568/804 |
| 3,843,606 | 10/1974 | Van Sorge | 568/804 |
| 3,873,628 | 3/1975 | Van Sorge | 568/804 |
| 3,968,172 | 7/1976 | Ichikawa et al. | 568/804 |
| 3,972,836 | 8/1976 | Van Sorge | 568/804 |
| 3,974,229 | 8/1976 | Van Sorge | 568/804 |
| 4,661,638 | 4/1987 | Battista et al. | 568/804 |

FOREIGN PATENT DOCUMENTS

| 1948607 | 9/1969 | Fed. Rep. of Germany . |
| 2135602 | 1/1972 | Fed. Rep. of Germany ...... 568/804 |
| 0497235 | 5/1972 | Japan . |

Primary Examiner—Werren B. Lone
Attorney, Agent, or Firm—Hedman, Gibson, Costigan & Hoare

[57] ABSTRACT

A catalyst precursor comprising a magnesium compound or material, optionally also containing other metal compounds, is activated for use by calcining at an elevated temperature in the presence of air or nitrogen, or under vacuum. The active catalyst which results may be used in processes for the ortho-alkylation of phenolic compounds, with good yields of and selectivity to the ortho-alkylated end product.

19 Claims, No Drawings

MAGNESIUM-CONTAINING CATALYST ACTIVATED UNDER VACUUM, IN NITROGEN, OR IN AIR, AND USE IN AN ORTHO-ALKYLATION PROCESS

This is a continuation of application Ser. No. 555,714 filed Nov. 28, 1983.

BACKGROUND OF THE INVENTION

Phenolic compounds which have an alkyl substituent in the ortho position on the ring are known to be useful as starting materials for the preparation of polyphenylene oxide (ether) resins. In general, such compounds are made by processes involving the vapor phase reaction of a phenolic compound and an alkyl alcohol in the presence of a catalyst. Various catalysts have been described in the patent literature.

For instance, processes for the ortho-methylation of a phenolic compound using magnesium oxide as a catalyst are disclosed by Hamilton in U.S. Pat. Nos. 3,446,856 and 3,479,410. Hamilton teaches that the magnesium oxide can be derived by the thermal decomposition of magnesium carbonate, basic magnesium carbonate or magnesium hydroxide. Van Sorge in U.S. Pat. No. 3,972,828, describes a catalyst consisting of powdered magnesium oxide in combination with an inert polymeric binder.

Still other catalysts are disclosed elsewhere in the patent literature. U.S. Pat. No. 3,873,628 describes a catalyst prepared by forming a mixture of magnesium oxide and manganese sulfate, heating to nearly complete dryness, and calcining at an elevated temperature to achieve activation. The mixture can be prepared using finely divided powders of the two compounds, or from an immersion of the magnesium oxide in an aqueous solution of manganese sulfate. Both U.S. Pat. Nos. 3,972,836 and 3,974,229 (also to Van Sorge) describe ortho-alkylation processes in which the catalyst comprises a mixture of magnesium and manganese oxides. In a preferred procedure, the catalyst is activated for use by heating it in the reactor in the presence of methanol vapor, prior to commencement of the alkylation reaction.

More recently, an ortho-alkylation process has been disclosed in which a catalyst comprising a magnesium compound is activated by calcining at an elevated temperature, in situ, in the presence of a feed stream of the alkylation reaction mixture. This is described in U.S. application Ser. No. 303,567, filed Sept. 18, 1981, belonging to the same assignee as herein.

INTRODUCTION TO THE INVENTION

The present invention is based on the discovery that a catalyst precursor comprising a source of magnesium, optionally also containing other catalytic metal or metal compounds, can be activated for subsequent use in ortho-alkylation reactions by a treatment comprising calcining at an elevated temperature in air or an inert gas such as nitrogen, or in a vacuum. The calcination can be performed outside the reactor, or in situ in the reactor prior to contacting with an alkylation feed mixture.

Alkylation reactions carried out in the presence of these catalysts result in a better yield of ortho-alkylated product, or alternatively, in better selectivity to the ortho-alkylated product, in comparison with a catalyst which has been calcined in situ in the presence of an alkylation feed.

Thus, one aspect of the invention comprises catalysts formed in the manner prescribed, and another aspect comprises use of the catalysts in a process for the ortho-alkylation of phenolic compounds. These aspects are more fully described as follows.

DESCRIPTION OF THE INVENTION

The catalyst precursor is generally provided in the form of a magnesium-containing material or compound, which may be used alone or in admixture with one or more additional metals or metal compounds that serve as co-catalytic ingredients.

Suitable magnesium compounds include magnesium carbonate and magnesium hydroxide, but other magnesium compounds capable of being converted to magnesium oxide at an elevated temperature without fusing or sintering may also be employed.

Suitable manganese-containing materials include basic magnesium carbonate. The term "basic magnesium carbonate" refers to materials represented by the formula

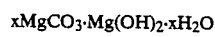

$$xMgCO_3 \cdot Mg(OH)_2 \cdot xH_2O$$

in which each x is independently a number average from about 3 to about 5.

In the preferred embodiments, the source of magnesium for the catalyst is basic magnesium carbonate, especially in the form of finely divided particles.

As indicated, the magnesium containing material or compound may be used in conjunction with additional metals or metal compounds in the catalyst precursor. These are selected from among compounds of other metals besides magnesium which, after calcining, exhibit co-catalytic activity with magnesium oxide. Compounds of manganese, copper, titanium and zinc are representative. Examples include manganese nitrate, manganese sulfate, manganese acetate, manganese bromide, manganese chloride, metallic copper, cupric nitrate, cuprous oxide, zinc nitrate, zinc oxide and titanium dioxide. The precursor may be prepared by mixing together dry powders of the respective metals or metal compounds, or if desired with use of more sophisticated techniques such as by precipitation of a compound of one of the metals, e.g., manganese hydroxide, in the presence of a suspension or slurry of the other, e.g., magnesium carbonate.

By way of further illustration, in one procedure a sequence is followed in which an aqueous solution of a manganese compound is added to a suspension of a magnesium compound in water, the two are mixed together, and a base, e.g., sodium hydroxide or ammonium hydroxide, is added gradually to cause precipitation of manganese hydroxide. In another procedure, which is also suitable, the aqueous mixture of magnesium and manganese compounds is heated to an elevated temperature to induce precipitation of the manganese compound without the use of a base.

Depending on how the catalyst precursor has been prepared, it may be desirable to dry it before calcination, to drive off any volatiles and to remove most of any moisture which may be present. Drying may be effected in any convenient manner, such as by blowing hot air over the particles, by heating in the presence of an applied vacuum, and so forth. In a preferred procedure, the particles of the precursor are placed in an open tray and heated in an oven at a temperature of from 100° to about 110° C., until less than about 2 percent by weight of volatiles remain.

Afterwards, the precursor is preferably treated to convert the particles to a free-flowing, finely divided form. This may be done, for instance, by grinding the particles through a wire mesh screen, for example, 16 to 20 mesh, U.S. Standard Sieve.

The finely divided precursor particles are then shaped into the desired physical form, which may be done using any suitable method or device. Illustratively, and preferably, the particles are shaped into tablets on a press, using standard tabletting equipment and procedures. If desired, however, the particles can be processed into cylinders, pellets or virtually any other shape known to those skilled in the art.

One or more supplementary materials which function as shaping aids or binders for the particles may also be added. In one procedure, a polyphenylene ether resin, such as described by Hay in U.S. Pat. Nos. 3,306,874 and 3,306,875, is compounded as a binder with the particles in an amount from about 0.1 up to about 20% by weight. Special mention is made of poly (2,6-dimethyl-1,4-phenylene ether)resin for this purpose. A polyphenylene ether copolymer may also be used instead. This is followed by the addition of a small amount, for instance, from 0.1 to 3.0% by weight, of powdered graphite as a shaping aid. The mixture is then tabletted.

After being shaped, the precursor is activated for use by a calcining treatment in which the particles are heated at an elevated temperature in air or nitrogen gas, or under vacuum. A temperature of at least 300° C., and preferably between about 350° and about 500° C., for a period of up to about 24 hours is usually sufficient, but temperatures as high as 550° C., may be used. The calcination may be and preferably is carried out before the catalyst is loaded into the reactor. Alternatively, calcination may be conducted in situ in the reactor after the catalyst precursor has been loaded and before the reaction is initiated.

The manner in which the precursor particles are heated is not critical. Thus, heat may be applied directly to the particles, as in an oven or upon contact with the heated walls of the reactor chamber, or through convection by contacting with air or nitrogen which has been preheated to the temperature of catalyst activation.

During calcination, minute pores form in the catalyst composite, thereby exposing more surface area. A surface area of at least 25 and especially from 25 to 450 square meters per gram of catalyst is desirable and will normally be achieved using the conditions described above.

The catalyst prepared in the aforementioned manner may be employed to effect or facilitate the ortho-alkylation of phenolic compounds, such as those having the formula

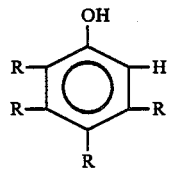

in which each R, independently, is a monovalent substituent selected from the group consisting of hydrogen, alkyl (preferably, $C_1$ to $C_{12}$ alkyl), phenyl, and alkyl substituted phenyl (preferably, $C_1$ to $C_{12}$ alkyl substituted phenyl).

The alkyl alcohol which is a co-reactant in the process is desirably a branched or linear saturated alcohol having up to about 16 carbon atoms, such as, for example, methyl, ethyl, propyl, isopropyl, butyl, isobutyl, tert.-butyl, amyl, isoamyl, hexyl, heptyl, octyl, nonyl, decyl, lauryl, cetyl, cyclohexyl, and the like. Especially preferred are alcohols having up to 6 carbon atoms, with methanol being the most preferred.

By way of illustration, a reaction feed mixture comprising the phenolic compound or compounds and an alkyl alcohol is vaporized and passed through a reactor heated to a temperature of at least 300° C., preferably from about 400° to about 500° C., which contains a catalyst prepared as described. For best results, it is advisable to use at least one mole of the alkyl alcohol, and preferably from one to three moles, for each ortho position on the phenol to be alkylated. For example, if phenol, which has two ortho hydrogens per molecule, is to be methylated to produce 2,6-xylenol, it is desirable to employ from two to six moles of methanol for each mole of phenol, the larger yields being obtained with use of higher ratios of methanol to phenol.

The ortho alkylation process can be carried out under a variety of reaction conditions of temperature, pressure, flow rate of reactants, vapor space velocity of reactants over catalyst, contact time of reactants with catalyst, length of catalyst feed, and so forth. Above a temperature of 500° C., however, decomposition of the reactants or products often becomes a problem, and such temperatures should be avoided.

Generally, the reaction conditions are regulated to minimize the amount of unreacted feed materials which must be recovered and reused, and to maximize the percentage of selectivity to the desired ortho-alkylated end product, that is, phenolic compounds having an alkyl substituent in the "2" or both the "2" and "6" positions on the ring.

While the reaction proceeds at atmospheric pressure, which is preferred, superatmospheric pressures or subatmospheric pressures can be used if desired.

The vapors issuing from the reactor are condensed, and the products are separated by conventional methods, such as crystallization or distillation.

DESCRIPTION OF THE SPECIFIC EMBODIMENTS

The invention is illustrated in the examples which appear below. A comparison with another catalyst type is included.

EXAMPLE 1

This example illustrates the preparation of a catalyst precursor and activation of the precursor by calcining under various conditions, including those in accordance with this invention.

In a vessel equipped with temperature measurement and stirring means, 518.9 grams of basic magnesium carbonate were added to 2000 milliliters of distilled water, with continuous mixing, to form a slurry. To this was added a 20 percent (by weight) solution of manganese nitrate in water, with the addition being carried out gradually over a period of 90 minutes. The resulting mixture, still comprising a suspension of basic magnesium carbonate particles, was stirred under a blanket of nitrogen, for 3 hours, with the temperature of the mixture being maintained at 80° C. for the entire period, during which a precipitate of manganese hydroxide formed. At the end of the period, the reation mixture was centrifuged to separate the solids. The solids were dried, then blended with poly(2,6-dimethyl-1,4-phenylene ether)resin (PPO ®, General Electric Company) in a 90:10 weight ratio. Powdered graphite in an amount of 0.5 percent by weight was added, and the resulting blend was tabletted on a press to form tablets having a dimension of 3/16 inch by ⅛ inch. This constituted the catalyst precursor.

The tablets were divided into four equal portions. One portion was not calcined, a second was calcined by heating at 500° C. overnight in air, a third was calcined by heating at 500° C. overnight in nitrogen, and the fourth was calcined by heating at 500° C. overnight in a vacuum.

EXAMPLE 2

The activated and non-activated catalysts prepared as described in Example 1 were evaluated in a process for the ortho-methylation of phenol and ortho-cresol to form 2,6-xylenol, using the reactor described below.

THE REACTOR

The Reactor comprises two stainless steel tubes, both disposed along a verticle axis, one of which has length of 15 inches (38.1 centimeters), the other of which has length of 24 inches (60.96 centimeters), and both of which have an inner diameter of ¾ inch (1.91 centimeters). The first functions as a vaporizer. The second is filled to a depth of two inches with glass beads serving as a support for the catalyst, and functions as a reactor. Both tubes are partially immersed in a fused salt bath, the first to a depth of 8 inches (20.3 cm), the second to a depth of 17 inches (43.2 cm). The first (vaporizer) and second (reactor) tubes are joined by a third tube, consisting of a two-inch long (5.1 cm) steel pipe connected at one end to an opening in the first tube 5 inches (12.7 cm) from its bottom, and at the other end to an opening in the second tube 14 inches (35.6 cm) from its bottom. The connector tube also passes through the fused salt bath.

In practice, a feed stream comprising the reactants is sent from a reservoir, through a metering pump, into the first (vaporizer) tube, where the feed stream is heated to a temperature high enough to volatilize the constituents. The vapors emitting from the vaporizer tube pass through the interconnecting pipe, which serves as a preheater to bring the vapors up the the temperature of the reactor tube. The vapors are fed from there to the reactor tube and the catalyst bed, where reaction takes place. Product vapors leave the bottom of the reactor tube through a stainless steel outlet tube, having an inner diameter of ⅜ inch (0.95 cm), and are led to a water-cooled condenser and receiver where they are liquified and recovered. The non-condensible materials are fed to an off-gas meter, where they can be measured.

In each of the present cases, the reactor was charged with 110 milliliters of catalyst (or catalyst precursor in one instance, as explained), then capped and placed in a 370° C. salt bath, immediately after which a stream of nitrogen gas was blown over the catalyst at a rate of 2 standard cubic feet per hour (SCFH). After a period of 15 minutes, the feed stream was introduced, which consisted of a 4:1 weight ratio of methanol to phenolics. The phenolics comprised a 60:40 weight ratio of phenol:ortho-cresol, containing about 20% water. A feed rate of 215 milliliters per hour was used, which was equivalent to a liquid hourly space velocity (LHSV) of 1.95. The reaction was conducted using standard pressure (1 atmosphere). The temperature was maintained at about 456° C. for the entire period. Periodically, the product stream was sampled and evaluated. The percentages of unreacted phenol and ortho-cresol, of 2,6-xylenol (the desired end product) and of 2,4,6-trimethyl phenol (a byproduct), as well as the selectivity to the desired end product were calculated, and the time weighted average results are reported below.

TABLE
COMPARISON OF CATALYSTS IN ORTHO-ALKYLATION PROCESS

| Catalyst by Type of Activation | Wt. % Phenol | Wt. % o-Cresol | Wt.% 2,6 | Wt. % 2,4,6 | Selectivity to 2,6, % |
|---|---|---|---|---|---|
| Vacuum | 2.00 | 17.30 | 73.89 | 6.96 | 10.5 |
| Nitrogen | 1.75 | 16.66 | 73.26 | 7.23 | 10.2 |
| Air | 2.63 | 25.98 | 66.86 | 3.92 | 17.1 |
| In Situ* | 3.23 | 21.21 | 68.16 | 6.83 | 10.1 |

*Prior Art Comparison

As can be seen, the best selectivity to 2,6-xylenol occurred with use of a catalyst which had been activated by calcining in air, in accordance with the invention. The selectivities in the other three cases are comparable, but the catalysts calcined in nitrogen and under vacuum, respectively, also according to the invention, resulted in higher yields of 2,6-xylenol than the comparison catalyst, which had been calcined in situ in the presence of the alkylation feed mixture.

All of the patents mentioned above are hereby incorporated herein by reference.

Other modifications and variations of the invention are possible and will occur to those skilled in the art in the light of this disclosure. Instead of methanol, other lower alkyl alcohols such as ethyl alcohol, propyl alcohol, butyl alcohol, or the like, can be used as a co-reactant. Instead of calcining outside the reactor, activation can be carried out in situ in the reactor, with use of the environments described, that is, vacuum, air or nitrogen. It is to be understood, therefore, that changes may be made in the particular embodiments shown which are within the scope of the invention defined by the appended claims.

We claim:
1. In a process for the selective ortho0alkylation of a phenolic compound preferentially to the para or meta alkylation by the vapor phase reaction of a feed mixture comprising an alkyl alcohol which is a branched or linear saturated alcohol having up to about 16 carbon atoms and a phenolic compound represented by the formula

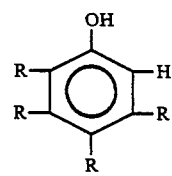

in which R is, independently, a monovalent substituent selected from the group consisting of hydrogen, alkyl having from 1 to 12 carbon atoms, phenyl, and alkyl-substituted phenyl in which the alkyl-substituent has from 1 to 12 carbon atoms, the improvement comprising conducting the reaction in the presence of a catalyst which is the calcined product derived by calcining a precursor comprising a source of magnesium and a source of manganese, said precursor formed by the steps comprising (i) providing an aqueous slurry of a magnesium-containing material selected from the group consisting of magnesium carbonate, basic magnesium carbonate and magnesium hydroxide, (ii) contacting the aqueous slurry with an aqueous solution of a soluble manganese compound under conditions which cause a precipitate of manganese hydroxide to form in the presence of the slurry, (iii) recovering the mixture of said magnesium-containing material and manganese hydroxide, which constitutes the precursor; and (iv) calcining the precursor recovered from step (iii) at an elevated temperature of at least 300° C. in an environment selected from the group consisting of air, an inert gas and vacuum, to activate it for subsequent use in an ortho-alkylation process, said process being conducted at temperature of from about 300° C. to about 550° C.

2. A process according to claim 1, in which the catalyst precursor has been calcined by heating in air.

3. A process according to claim 1, in which the catalyst precursor has been calcined by heating in a vacuum.

4. A process according to claim 1, in which the phenolic compound is ortho-cresol.

5. A process according to claim 1, in which the alkyl alcohol is methanol.

6. A process according to claim 1, in which the magnesium-containing material is basic magnesium carbonate.

7. A process according to claim 1, in which the magnesium compound is magnesium carbonate or magnesium hydroxide.

8. A process according to claim 1, in which the catalyst precursor has been calcined at a temperature of at least 500° C.

9. A process according to claim 8, in which the calcining temperature is between about 350° and about 550° C.

10. A process according to claim 1, in which the catalyst also includes a binder and/or shaping aid.

11. A process according to claim 10, in which the binder is a polyphenylene ether resin.

12. A process according to claim 11, in which the polyphenylene ether resin is poly(2,6-dimethyl-1,4-phenylene)ether.

13. A process according to claim 10, in which the shaping aid is particulate graphite.

14. A process according to claim 1, in which the catalyst precursor has been calcined by heating in an inert gas comprised of nitrogen.

15. A process according to claim 1, in which the catalyst precursor is calcined outside of the reactor.

16. A process according to claim 1, in which the catalyst precursor has been calcined in situ in the reactor prior to contacting said catalyst with an alkylation feed mixture.

17. A process according to claim 1, in which the reaction temperature is from about 300° C. to about 500° C.

18. A process according to claim 17, in which the reaction temperature is from about 300° C. to about 400° C.

19. A process according to claim 17, in which the reaction temperature is from about 400° C. to about 500° C.

* * * * *